(12) United States Patent
Schaldach, Jr.

(10) Patent No.: US 6,245,092 B1
(45) Date of Patent: Jun. 12, 2001

(54) HIGHLY INTEGRATED ELECTRONIC CIRCUIT, IN PARTICULAR FOR USE IN HEART PACEMAKERS

(75) Inventor: Max Schaldach, Jr., Berlin (DE)

(73) Assignee: Biotronik Mess- und. Therapiegeraete GmbH & Co., Ingenieurbuero Berlin (DE)

( * ) Notice: Subject to any disclaimer, the term of this patent is extended or adjusted under 35 U.S.C. 154(b) by 0 days.

(21) Appl. No.: 09/313,086

(22) Filed: May 17, 1999

(30) Foreign Application Priority Data

May 15, 1998 (DE) .............................. 198 21 857

(51) Int. Cl.[7] ...................................................... A61N 1/00
(52) U.S. Cl. ...................................................... 607/1
(58) Field of Search ................................ 607/1, 36, 37, 607/9, 5; 361/749, 803; 623/11

(56) References Cited

U.S. PATENT DOCUMENTS

| | | |
|---|---|---|
| 5,159,751 | 11/1992 | Cottingham et al. . |
| 5,224,023 | 6/1993 | Smith et al. . |
| 5,362,656 | 11/1994 | McMahon . |
| 5,386,341 | 1/1995 | Olson et al. . |
| 5,434,362 | 7/1995 | Klosowiak et al. . |
| 5,645,586 | 7/1997 | Meltzer . |
| 5,717,556 | 2/1998 | Yanagida . |
| 5,749,910 | 5/1998 | Brumwell et al. . |

FOREIGN PATENT DOCUMENTS

| | | |
|---|---|---|
| 1 916 876 | 1/1965 | (DE) . |
| 1 591 513 | 2/1970 | (DE) . |
| 1 932 380 | 1/1971 | (DE) . |
| 33 18 717 | 5/1984 | (DE) . |
| 38 09 237 | 10/1988 | (DE) . |
| 40 17 217 | 12/1991 | (DE) . |
| 92 01 519 | 5/1992 | (DE) . |
| 92 01 662 | 7/1992 | (DE) . |
| 296 22 830 U | 10/1997 | (DE) . |
| 1 424 436 | 12/1966 | (FR) . |

OTHER PUBLICATIONS

Patent abstracts of Japan, 05–013967, E–1373, May 31, 1993, vol. 17, No. 183.

Patent abstracts of Japan, 56–105659, E–82, Nov. 17, 1981, vol. 5, No. 179.

Patent abstracts of Japan, 01–295454, E–889, Feb. 15, 1990, vol. 14, No. 82.

*Primary Examiner*—Scott M. Getzow
(74) *Attorney, Agent, or Firm*—Browdy & Neimark

(57) ABSTRACT

A highly integrated electronic circuit is provided with a flexible substrate which has a component side and an insulating bottom side as well as with an arrangement, corresponding to the circuit function, of active and passive electronic components. These are mounted on bond pads of the substrate and connected by strip conductors, corresponding to the circuit function.

The substrate is folded along a fold portion so that the sections of the substrate, which are on both sides of the fold portion and equipped with components, are approximately parallel and close to each other.

24 Claims, 2 Drawing Sheets

HIGHLY INTEGRATED ELECTRONIC CIRCUIT, IN PARTICULAR FOR USE IN HEART PACEMAKERS

BACKGROUND OF THE INVENTION

1. Field of the Invention

The invention relates to a highly integrated electronic circuit, in particular for use in heart pacemakers, defibrillators and the like, comprising a flexible substrate, which has a component side and an insulating bottom side, and an arrangement, corresponding to the circuit function, of active and passive electronic components on the component side of the substrate which are fixed to bond pads of the substrate and connected by strip conductors on the substrate, corresponding to the circuit function.

2. Background Art

As for the background of the invention it is to be noted that in highly integrated electronic circuits, various types of components, i.e. active and passive electronic components, are electrically connected to each other. The substrate consists of an electrically insulating, dielectric material on which bond pads for bonding the components and electric strip conductors for connecting the components to each other are available. Further bond pads can be provided as interfaces for the connection of the highly integrated electronic circuit to external components, such as a power supply, telemetry components and the like. Thus the highly integrated electronic circuit is incorporated into the surrounding field of a certain appliance. Bonding the pads takes place for instance by soldering.

In particular when used in heart pacemakers, defibrillators and the like, miniaturization of these highly integrated electronic circuits plays a very important part. The overall size of these implantable medical devices can be reduced as the compactness of the circuit grows, which, from a medical point of view, leads to simplification of the necessary surgical operations and improved tolerance by the patient.

Fundamentally, the minimization of the number of different manufacturing operations is an object to be achieved with a view to manufacturing rationalization and the simultaneous increase of reliability which is absolutely necessary with these devices.

As regards the prior art, conventional highly integrated electronic circuits are based on rigid ceramic substrates. So as to increase the packing density of the components, their size can be reduced and bonding can be performed in as space-saving a manner as possible. In this connection, SMD (=surface-mounted-device) technology must be cited, in which the surface bonded components no longer have connecting pins. It is also known to use several strip conductor levels one above the other in a substrate as a measure of increasing the packing density.

Further, the prior art teaches circuits which are constructed on flexible plastic substrates. By means of lithographic processes, very narrow strip conductor structures can be applied to such flexible substrates at reduced distances, which can contribute considerably to the miniaturization of the circuit.

U.S. Pat. No. 5,386,341 explicitly illustrates the use of a flexible substrate folded in a U-shape, a rigidizer plate being positioned in the notch of the U of the substrate. Semiconductor components rest on the top side of this sandwich structure, whereas the bottom side is connected via soldering spots to a higher order circuit board. Different temperature coefficients of expansion of the circuit board and the electronic components are compensated by the flexible substrate.

It is further known from U.S. Pat. No. 5,362,656 to wrap a flexible circuit around a rigid metal substrate, the conductors of the flexible circuit being connected to an integrated circuit which is mounted on the top side of the substrate. The flexible circuit has a plurality of metal pads located adjacent to the bottom side of the substrate. The integrated circuit is coupled to the metal pads by way of signal lines in the flexible circuit. The pads can be soldered to a printed circuit board to electrically couple the integrated circuit to the board.

SUMMARY OF THE INVENTION

It is an object of the invention to create a highly integrated electronic circuit optimized as to space and manufacturing requirements, in particular with a view to its use in heart pacemakers and defibrillators.

This object is attained by the invention, according to which the substrate is folded along a fold portion so that the sections of the substrate, which are on both sides of the fold portion and equipped with components, are approximately parallel and close to each other. The highly integrated electronic circuit is very compact due to the folding and the use of a flexible substrate which is very thin as a rule. Folding takes place without any mechanically supporting intermediate layer, which is for the benefit of the compactness of the circuit. The solely unilateral application of electronic components on the component side of the substrate permits a single bonding process to be used in a single manufacturing operation. Further details will become apparent from the description of the exemplary embodiment.

Advantageous improvements of the subject matter of the invention will become apparent from the ensuing description of an exemplary embodiment of the invention, taken in conjunction with the drawings.

DESCRIPTION OF THE PREFERRED EMBODIMENT

Figure 1:
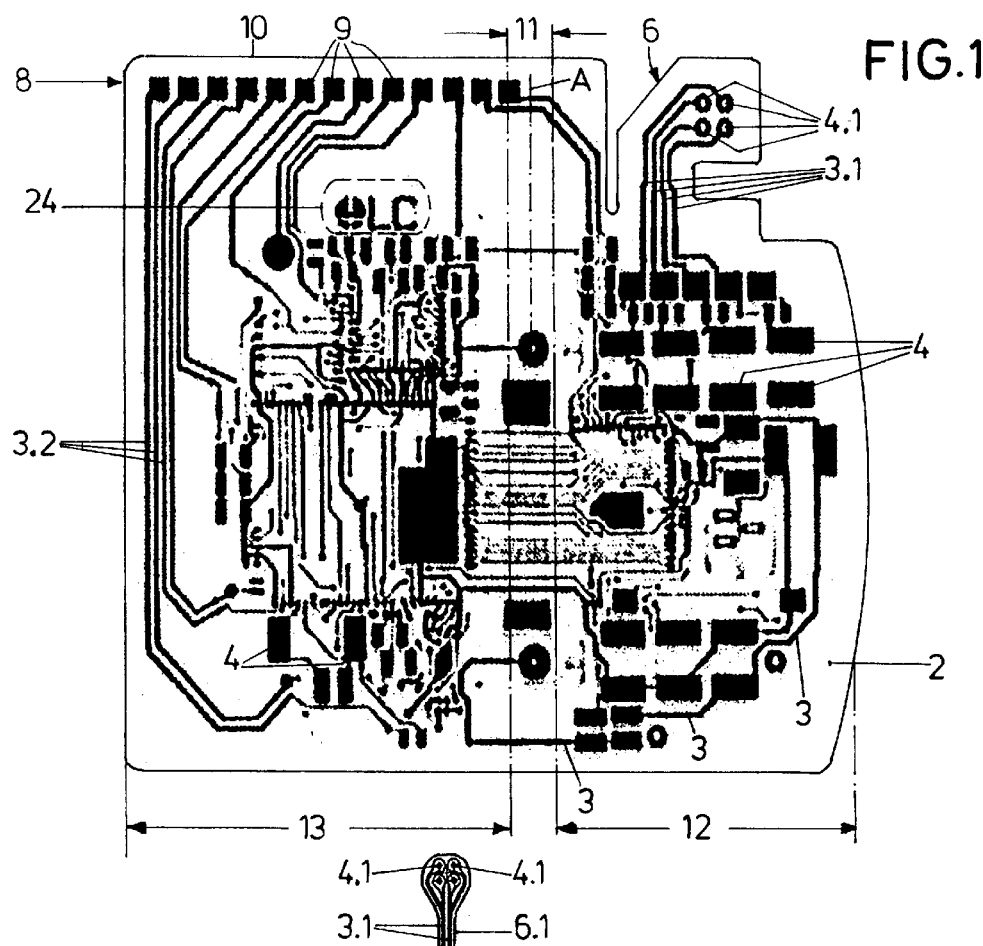
FIG. 1 is a plan view of the component side of a flexible substrate prior to the insertion of components.

As seen in FIG. 1, a substrate 1 of flexible plastic film comprises, on its component side 2 seen in the drawing, an arrangement, corresponding to the circuit function, of metal strip conductors 3 and bond pads 4 applied by lithography or laser technique (or by a combination of both methods). The bond pads 4 are rectangles, squares, circles or circular rings of enlarged dimensions as opposed to the strip conductors 3. Components 5 are soldered on these bond pads 4 in a manner still to be described; they are thus connected to each other via the strip connectors 3, corresponding to the circuit function.

Figure 2:
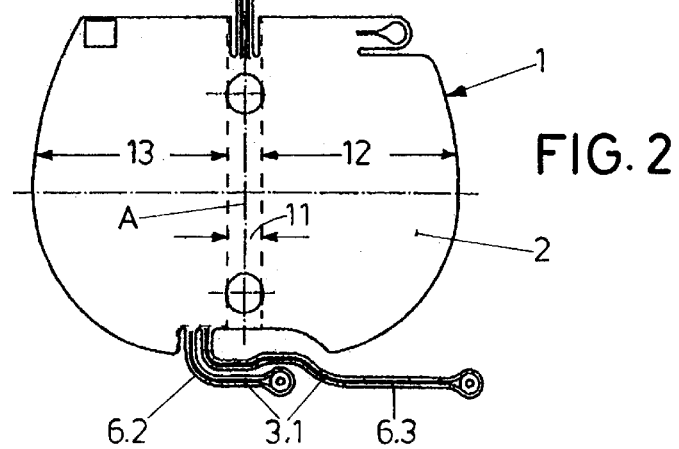
FIG. 2 is a diagrammatic plan view of a second embodiment of a substrate.

As further seen in FIG. 1, in this exemplary embodiment, the substrate 1 is provided with a connection tongue 6, which is integrally attached in the shape of an L and consequently flexible as the substrate 1, and on which four strip conductors 3.1 lead to bond pads 4.1 where an electric, vacuum-tight duct through the vacuum-tight casing of the pacemaker can be connected for bonding the electrode plug. A connection tongue 6.1 of this type having strip conductors 3.1 and bond pads 4.1 and serving for the same purpose is illustrated in FIG. 2 as a piece attached in a straight line and having a widened end on which a pad is simultaneously provided for the bonding between the casing and the circuit. Further elongated connection tongues 6.2 and 6.3 are integrally molded on the opposite side, via which a battery 7 (FIG. 3) can be coupled to the substrate 1 for the power supply of the highly integrated electronic circuit.

FIG. 1 further shows a row 8 of test bond pads 9 placed on an edge 10 of the substrate 1. Via various strip conductors 3.2, the test bond pads 9 are looped through to various points of the circuit. After component insertion of the substrate 1, the operatability of the circuit thus created can be tested very rapidly via the test pads 9 by means of a multi-fingered contact arm. Afterwards the portion of the substrate 1 that carries the test bond pads 9 and the strip conductors 3.2 can be removed so that the substrate exhibits a contour which is approximately symmetrical about the axis A of FIG. 1. This means that the left part of the substrate 1 seen in FIG. 1 terminates in the same semi-circular shape as the right part thereof. As for the test bond pads 9, it must be said for completion that they are applied unilaterally and formed in accordance with a standardized test bond structure. They render the complicated approach to individual test bond spots within the circuit superfluous and permit standardization throughout varying product lines.

Figure 3:
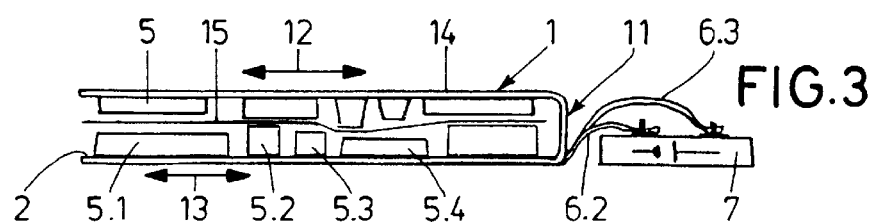
FIG. 3 is a diagrammatic lateral view of a highly integrated electronic circuit in a folded condition of the flexible substrate after component insertion.

In order to reduce the space requirement of the entire highly integrated electronic circuit to the dimension of a bilaterally equipped, highly integrated electronic circuit in spite of the only unilateral insertion on the component side 2 and the thus resulting active surface of the substrate of basically twice the size, the flexible substrate is folded approximately centrally about the axis A—as seen in FIG. 3—so that the sections 12, 13 of the substrate lying on both sides of the fold portion 11 face each other by their component sides. The passive bottom side 14 of the substrate 1 forms the insulation of the highly integrated electronic circuit toward the casing and further component parts of the heart pacemaker equipped therewith. In the approximately U-shaped configuration of the circuit seen in FIG. 3, the sections 12, 13 equipped with components 5 that are turned inwards, such as ICs 5.1, diodes 5.2, capacitors 5.3 or resistors 5.4, are close to each other. Integrated covering of the circuit is accomplished by this arrangement. For proper electric separation between the parallel sections 12, 13 of the substrate 1 on the component side 2 to be ensured, an insulating layer 15, for instance in the form of a non-conductive film sheet, is placed in between.

By analogy to the insulating layer 15, a component part of the heart pace-maker equipped with the highly integrated electronic circuit can also be placed between the two sections 12, 13 of the folded substrate, which is not shown in FIG. 3. This may for instance be a telemetry coil, which otherwise needs special implementation as a part lying outside the highly integrated electronic circuit. In the case of the positioning, discussed above, of the telemetry coil, the latter's connection lines are soldered to a corresponding bond pad in the proximity of the fold portion 1—for instance the bond pads 4.1 in FIG. 1—and then the substrate equipped with components is folded with the telemetry coil placed in between. In this case the insulating layer 15 is superfluous, since the coil is insulated anyway and can additionally be embedded in a plastic film.

Figure 4:
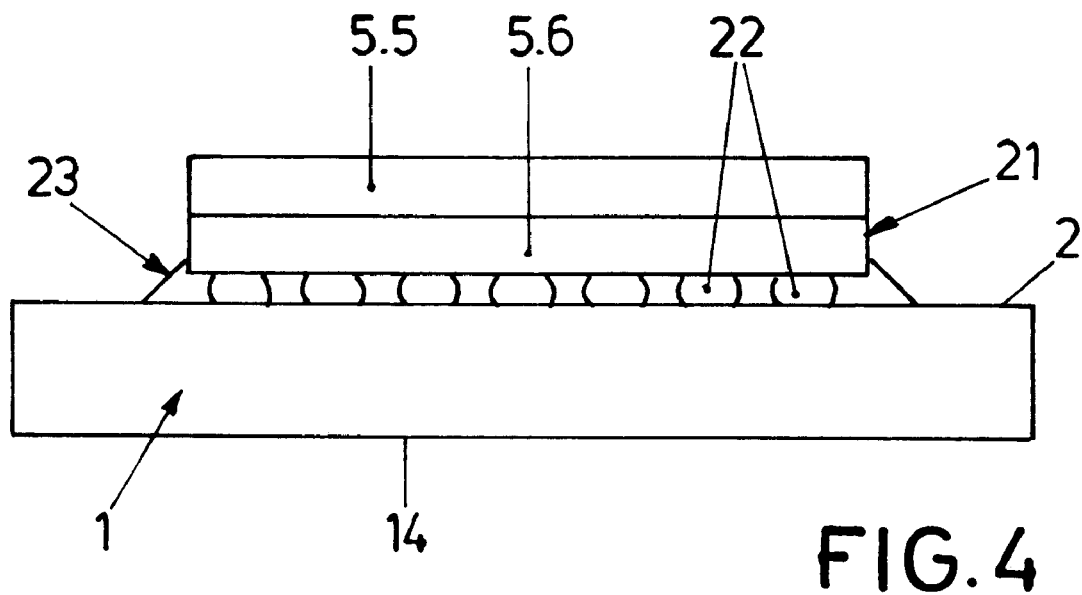
FIG. 4 is a diagrammatic detailed view of the application of active components on the substrate with passive components being interconnected.
Figure 5:
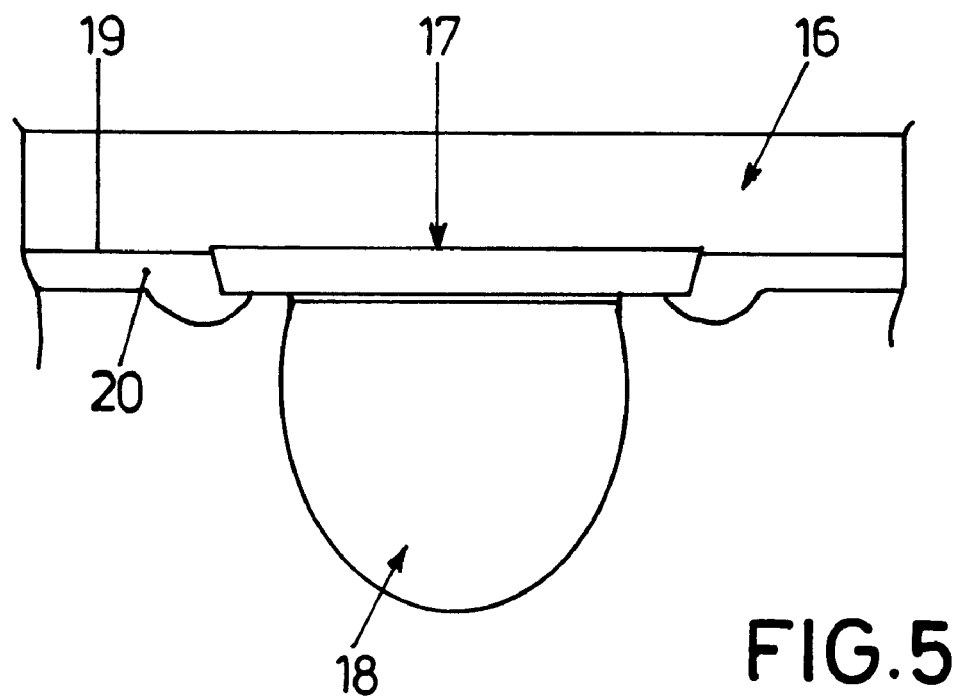
FIG. 5 is an even more detailed diagrammatic illustration of a soldering spot on an active component.

As diagrammatically outlined in FIGS. 4 and 5, the use of semiconductor components 5.5 in the so-called chip scale package technology can contribute to the further reduction of the space requirement and the number of manufacturing steps for the highly integrated electronic circuit. In this case, semiconductor components are no longer applied with their active side, to be bonded for instance via miniature wires, turned away from the substrate 1, but with their active side turned towards the substrate 1. Fixing and bonding takes place by means of solder drops as seen in FIG. 5, where the active silicon wafer layer 16 of the semiconductor chip is provided with a pad 17 on which a solder drop 18 is placed. The bottom side 19 of the silicon wafer layer 16 and the edge of the pad 17 are insulated by a benzocyclobutene layer 20 which is necessary for the lithography. The pads 17 or corresponding bond pads of the specified components 5 are provided with solder drops 18 in the way seen in FIG. 5 and placed on the unfolded plane substrate 1. By heating the prepared arrangement once, soldering of all components 5 is effected by a uniform solder-bonding process and in a single production step. In this connection attention is drawn to the fact that the bond pads 4 on the substrate 1 may be provided with corresponding solder drops instead of the components 5, that the components are placed subsequently, and that simultaneous soldering of all components can take place again by thermal effect. Instead, the soldering process can also be replaced by a gluing process (to avoid the lead in the solder).

The chip scale package technology discussed in the foregoing has the further advantage of increasing the compactness of the circuit. On the one hand, this is due to the fact that fitting protective casings over the semiconductor components used is unnecessary, since it is not the sensitive, active side, but only the insensitive, passive side that lies open, turned away from the substrate 1 and unprotected. On the other hand, the chip scale package technology offers the possibility to connect a semiconductor component 5.5, as seen for example in FIG. 4, and a substrate 1 by way of a functional re-wiring layer 21 placed in between and having a passive component, such as a resistor 5.6, integrated therein. Consequently, an active component 5.5 can rest on the substrate 1 via the re-wiring layer 21 provided with layers of passive components. The connection is again effected by way of soldering spots which are designated as "flip chip bumps" in the technical language.

These soldering spots 22 together with the bottom side of the passive component 5.6 are embedded in an epoxy resin layer 23.

The integration, mentioned above, of passive resistors or other passive components as connecting elements ensures the manufacture thereof by any technology independent of the manufacture of the substrate and the subsequent attachment thereof in a single step of production. Moreover, a modular design becomes feasible for deviating highly integrated electronic circuits, in which the attachment of further semiconductor components of different specifications to the passive components only requires the use of another passive component in the connection with the active component, however not another strip conductor design on the substrate 1.

Doing without several thermal processes during component insertion, which regularly lead to modifications of the properties of the substrate, as well as the increased precision of the strip conductors due to their lithographic structuring permit the parallel, multiple-panel manufacture of several highly integrated electronic circuits and the subsequent separation. Conventional rigid ceramic substrates only allow single-panel manufacture due to the reduced precision.

As regards the substrate (1), its typical dielectric layer thickness is in the range of approximately 50 μm. So as to obtain sufficient mechanical stability, another rigidifying layer of a thickness of approximately 400 μm is provided, which also provides for the electric insulation of the bottom side 14 of the substrate 1. As a rule the material of the substrate is polyimide.

Once again referring to FIG. 1, it must be said for completion that the substrate 1 is directly provided with a radiographically visible mark 24—in this case in the form of a logo of a company and the combined letters "LC". Thus an X-ray mark is directly integrated in the substrate. This has not been possible with the customary rigid highly integrated electronic circuits, since the X-ray mark exhibits substantial space requirements, which has not been accepted given the scarce substrate surface available. In this regard, the X-ray mark has so far been integrated by a separate operation into another component of for instance a heart pacemaker.

What is claimed is:

1. A highly integrated electronic circuit for use in heart pacemakers, defibrillators and the like, implementing a circuit function and comprising:
   a flexible substrate (1) having a component side (2) and an insulating bottom side (14); and
   an arrangement, corresponding to the circuit function, of active and passive components (5) on the component side (2) of the substrate (1), which are mounted on bond pads (4) of the substrate (1) and connected via strip conductors (3) on the substrate (1) corresponding to the circuit function, wherein the substrate (1) is folded along a fold portion (11) so that sections (12, 13) of the substrate (1), which are on both sides of the fold portion (11) and equipped with components (5) are approximately parallel and close to each other, and the substrate (1) is provided with standardized test bond pads (9), which are removable prior to said folding of the substrate (1) equipped with components.

2. A circuit according to claim 1, wherein the fold portion (11) is disposed approximately centrally relative to an overall surface of the substrate (1) so that the circuit has an approximately U-shaped configuration.

3. A circuit according to claim 1, wherein the component side (2) of the substrate (1) lies inside in the folded condition.

4. A circuit according to claim 3, wherein an insulating layer (15) is placed between the components (5) turned toward each other on the respective sections (12, 13) of the substrate (1).

5. A circuit according to claim 1, wherein the substrate (1) is provided with integrally attached flexible confection tongues (6) for connection of the circuit to external components (7).

6. A circuit according to claim 1, wherein the test bond pads (9) are arranged in a row (8) on an edge (10) of the substrate (1).

7. A circuit according to claim 1, wherein a radiographically visible mark (24) is disposed on the substrate (1) preferably on a foldable tongue which stands out from an edge of the substrate.

8. A circuit according to claim 1, wherein all the components (5) on the component side (2) are mounted by a uniform bonding process in a single manufacturing operation.

9. A circuit according to claim 8, wherein the components (5) are mounted by one of soldering and gluing.

10. A circuit according to claim 1, wherein active components (5.5) are disposed in a pickaback manner on passive components (5.6) which function as connection elements between the respective active component (5.3) and the substrate (1).

11. A circuit according to claim 1, comprising a structuring of the strip conductors (3) by lithography.

12. A circuit according to claim 1, comprising a structuring of the strip conductors (3) by laser technique.

13. A highly integrated electronic circuit for use in heart pacemakers, defibrillators and the like, implementing a circuit function and comprising:
   a flexible substrate (1) having a component side (2) and an insulating bottom side (14);
   an arrangement, corresponding to the circuit function, of active and passive components (5) on the component side (2) of the substrate (1), which are mounted on bond pads (4) of the substrate (1) and connected via strip conductors (3) on the substrate (1) corresponding to the circuit function, wherein the substrate (1) is folded along a fold portion (11) so that sections (12, 13) of the substrate (1), which are on both sides of the fold portion (11) and equipped with components (5), are approximately parallel and close to each other; and
   at least one external component placed between the components (5) with which the sections (12, 13) of the folded substrate (1) are equipped.

14. A circuit according to claim 13 wherein the at least one external component is a telemetry coil of an implantable cardiological device.

15. A circuit according to claim 13, wherein the fold portion (11) is disposed approximately centrally relative to an overall surface of the substrate (1) so that the circuit has an approximately U-shaped configuration.

16. A circuit according to claim 13, wherein the component side (2) of the substrate (1) lies inside in the folded condition.

17. A circuit according to claim 16, wherein an insulating layer (15) is placed between the components (5) turned toward each other on the respective sections (12, 13) of the substrate (1).

18. A circuit according to claim 13, wherein the substrate (1) is provided with integrally attached flexible connection tongues (6) for connection of the circuit to external components (7).

19. A circuit according to claim 13, wherein a radiographically visible mark (24) is disposed on the substrate (10) preferably on a folded tongue which stands out from an edge of the substrate.

20. A circuit according to claim 13, wherein all the components (5) on the component side (2) are mounted by a uniform bonding process in a single manufacturing operation.

21. A circuit according to claim 20, wherein the components (5) are mounted by one of soldering and gluing.

22. A circuit according to claim 13, wherein active componets (5.5) are disposed in a pickaback manner on passive components (5.6) which function as connection elements between the respective active component (5.5) and the substrate (1).

23. A circuit according to claim 13, comprising a structuring of the strip conductors (3) by lithography.

24. A circuit according to claim 13, comprising a structuring of the strip conductors (3) by laser technique.

* * * * *